United States Patent
Matsuda et al.

(10) Patent No.: US 6,918,394 B2
(45) Date of Patent: Jul. 19, 2005

(54) DEVICE FOR PREVENTING SLEEP APNEA

(75) Inventors: Narihiko Matsuda, Kobe (JP); Masayoshi Furuya, 1-6-22, Kido, Kawachi Nagano-shi, Osaka-fu (JP)

(73) Assignees: Medical treatment corporate judicial person Matsuda dentist's office, Kobe (JP); Masayoshi Furuya, Osaka-fu (JP)

(*) Notice: Subject to any disclaimer, the term of this patent is extended or adjusted under 35 U.S.C. 154(b) by 218 days.

(21) Appl. No.: 10/254,684

(22) Filed: Sep. 26, 2002

(65) Prior Publication Data
US 2003/0056785 A1 Mar. 27, 2003

(30) Foreign Application Priority Data

Sep. 27, 2001 (JP) .................................... 2001-296691

(51) Int. Cl.[7] .................................................. A61F 5/56
(52) U.S. Cl. ...................... 128/848; 128/858; 602/902; 606/199; 606/204.25
(58) Field of Search .............................. 128/846, 848, 128/857–858; 602/902; 606/199, 204.25

(56) References Cited

U.S. PATENT DOCUMENTS

| | | | | |
|---|---|---|---|---|
| 2,999,232 A | * | 9/1961 | Wilson | .................... 340/575 |
| 4,201,205 A | * | 5/1980 | Bartholomew | .......... 128/205.25 |
| 4,330,272 A | * | 5/1982 | Bergersen | ........................ 433/5 |
| 5,787,894 A | * | 8/1998 | Holt | ............................ 128/848 |

OTHER PUBLICATIONS

Patent Abstracts of Japan, Publ. No. 2000-116662, Apr. 25, 2000, "Auxiliary Device for Ensuring External Respiratory Tract", Kinoshita Yukihiro & JP–2000–116662.

Patent & Utility Model Gazette DB, Translation of Claims of JP–09–502910–A (Mar. 25, 1997), including Fig. 1.

Respironics Catalogue of a mask device entitled "Virtuoso LX SmartCard System".

* cited by examiner

*Primary Examiner*—Michael A. Brown
(74) *Attorney, Agent, or Firm*—Birch, Stewart, Kolasch & Birch, LLP

(57) ABSTRACT

The present invention provides a device which prevents loud snoring and apnea during sleep so as not to cause discomfort to a user as much as possible. Stoppers 4 such as belts or straps having predetermined elasticity are attached to both right and left sides of a lower jaw fitting piece 3 which fits the both sides of the lower jaw, the lower jaw 2 is pushed forward via the lower jaw fitting piece 3 by setting and hanging the stoppers 4 on the nose or head of the face side, whereby occurrence of apnea and loud snoring during sleep is prevented.

9 Claims, 4 Drawing Sheets

(a)           (b)

DEVICE FOR PREVENTING SLEEP APNEA

BACKGROUND OF THE INVENTION

1. Field of the Invention

The present invention relates to a device for preventing sleep apnea in the field of oral medical treatment.

2. Description of the Related Art

There are surprisingly many people who snore during sleep, and some of them suffer from sleep apnea.

Snoring is caused by muscle relaxation during sleep, and when the jaw muscle relaxes, the lower jaw moves rearward and moves the tongue to the rear side of the oral cavity, whereby the breathing airway of the pharynx is narrowed, the breathing airflow eddies, the velum and the surrounding soft muscle vibrates and causes a sound phenomenon called snoring.

When the lower jaw moves rearward and the lingual root falls and closes the opening of the airway, an air blockage occurs, that is, an apnea condition may be caused.

Therefore, for people who snore loudly or suffer from sleep apnea, a positive pressure breathing apparatus for feeding a fixed amount of air by applying a nasal mask and resin appliances to be fitted on the upper teeth and lower teeth in the oral cavity to position the lower jaw forward have been generally known.

However, in the former case, it is necessary that a slightly large mask is applied on the nose, and also, an air hose or air supplier is required.

Furthermore, in the latter case, although the appliances are preferable since they are small and are compactly housed inside the oral cavity, the upper and lower jaws become difficult to move, and this is distressing for a user and causes an ache in the mandibular joint due to long periods of use.

Other than these, an aboral apparatus has been generally known, which applies a so-called jaw lift method for artificial respiration by lifting the lower jaw of a patient in a strained condition and supports the lower jaw from both lower sides in a condition where the patient lies on his/her back to prevent the airway from closing during sleep.

However, since the lower jaw is supported from both sides during sleep, a user cannot roll over during sleep and cannot freely move while he/she lies on his/her back, so that this method is distressing for the user.

SUMMARY OF THE INVENTION

The present invention has been made in view of the abovementioned circumstances, and in order to solve the abovementioned problems, an object of the invention is to provide a device for preventing sleep apnea formed so that stoppers such as belts or straps having predetermined elasticity are attached to both right and left sides of a lower jaw fitting piece which fits the lower jaw, and these stoppers are set and hung on the nose or head of the face side, whereby the lower jaw is pushed forward via the lower jaw fitting piece in order to prevent apnea and snoring during sleep.

Since the device for preventing sleep apnea is formed so as to push the lower jaw forward via the lower jaw fitting piece, it can be prevented that the lower jaw moves rearward and the lingual root falls and closes the breathing airway during sleep, and therefore, loud snoring and sleep apnea can be prevented.

Furthermore, another object of the invention is to provide a device for preventing sleep apnea constructed so that the lower jaw fitting piece is formed into a U shape along the lower jaw, at least the contact portion to the lower jaw is formed from a soft material, and a stopping portion is provided at the side circumference of the lower jaw fitting piece to stop the end of the stopper.

Thereby, a user can freely roll over during sleep, and since the contact portion to the skin at the lower jaw and nose is formed from a soft material, skin discomfort can be prevented, and furthermore, adjustments to pull the stoppers in desired appropriate directions via a plurality of stopping portions can be made depending on a user.

Still another object of the invention is to provide a device for preventing sleep apnea constructed so that contact stopping portions shaped into hooks for stopping on the rear edges of the lower jaw are formed at the both ends of the lower jaw fitting piece.

Thereby, the lower jaw can be securely pushed forward via the lower jaw fitting piece.

Furthermore, still another object of the invention is to provide a device for preventing sleep apnea constructed so that the section of the lower jaw fitting portion is roughly L-shaped for setting on the rear edges of the lower jaw in a fitting condition.

Thereby, the lower jaw fitting portion can be prevented from coming off the rear edges of the lower jaw even when the stoppers are pulled.

Furthermore, still another object of the invention is to provide a device for preventing sleep apnea in which the lower jaw fitting piece is inserted an aluminum material, a thermoplastic resin, or an engineering plastic material in it.

Thereby, the lower jaw fitting piece can be made thin and light in weight, and made easy to use for a user. Particularly, an aluminum plate or thermoplastic resin are preferable since they can be bent into a desired shape so as to be suitable to the lower jaw of a user.

Furthermore, still another object of the invention is to provide a device for preventing sleep apnea constructed so that a holder is shaped into a nasal mask or a bridge surrounding the nose, slit-shaped holding portions are symmetrically provided at the upper and lower portions of both sides of the holder, the other ends of the abovementioned stoppers of the lower jaw fitting piece are connected to the lower holding portions, and soft hanging members such as rubber belts or rubber straps to be hung on the ears or head are connected to the upper holding portions.

Thereby, stoppers such as soft belts or straps having elasticity of the lower jaw fitting piece can be tensioned and set onto the ears or head through the nose via a fixing holder tool, whereby the lower jaw fitting piece can be stably pushed toward the upper jaw side and forward.

Furthermore, still another object of the invention is to provide a device for preventing sleep apnea constructed so that the other ends of the stoppers of the lower jaw fitting piece are set on a mask portion of a positive pressure breathing apparatus.

Thereby, use in combination with a positive pressure breathing apparatus is possible, the stoppers of the lower jaw fitting piece can be set on the mask portion of a positive pressure breathing apparatus to fix the mask, and the lower jaw fitting piece is also fixed.

Further scope of applicability of the present invention will become apparent from the detailed description given hereinafter.

DETAILED DESCRIPTION OF THE PREFERRED EMBODIMENTS

A device for preventing sleep apnea according to the invention is characterized in that, in order to prevent occurrence of apnea and snoring during sleep, stoppers such as belts or straps having predetermined elasticity are attached to both right and left sides of a lower jaw fitting piece which fits the lower jaw, and these stoppers are set and hung on the nose and head of the face side to push the lower jaw forward via the lower jaw fitting piece.

Figure 1:
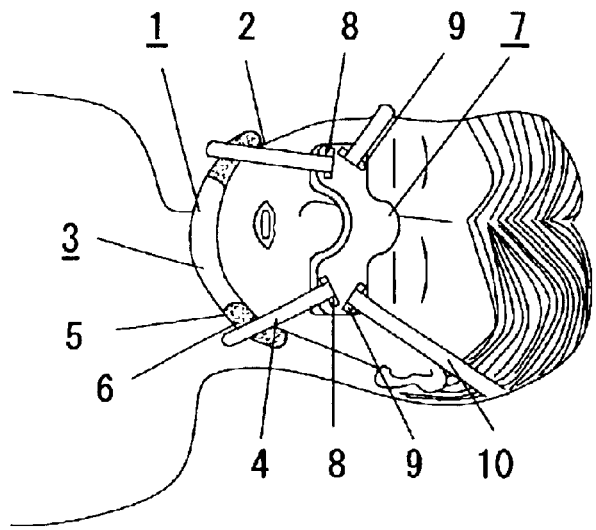
FIG. 1 is a perspective view for explaining use of an embodiment of the invention.

Device 1 for preventing sleep apnea is of an aboral apparatus, which is constructed so that a lower jaw fitting piece 3 is fit along the lower jaw 2 of a user as shown in FIG. 1, and stoppers 4 are attached to the lower jaw fitting piece 3 so as to push the lower jaw 2 forward.

Figure 4:
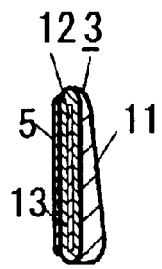
FIG. 4 is a side sectional view of the lower jaw fitting piece of the same.

The lower jaw fitting piece 3 can be bent into, for example, as shown in FIG. 4, a U-shape having an inclined inner circumferential surface along the lower jaw 2, particularly from the lower jaw rear edges to the lower jaw lower edge, and hanging stopping portions 5 are provided at proper positions at the front and rear portions of the lower jaw fitting piece, and the ends of soft stoppers 4 such as rubber belts or rubber straps having predetermined elasticity are connected to the stopping portions 5 by connecting means 6 such as velvet fasteners, metal eyelets, or hooks so as to push the lower jaw 2 forward.

Figure 2:
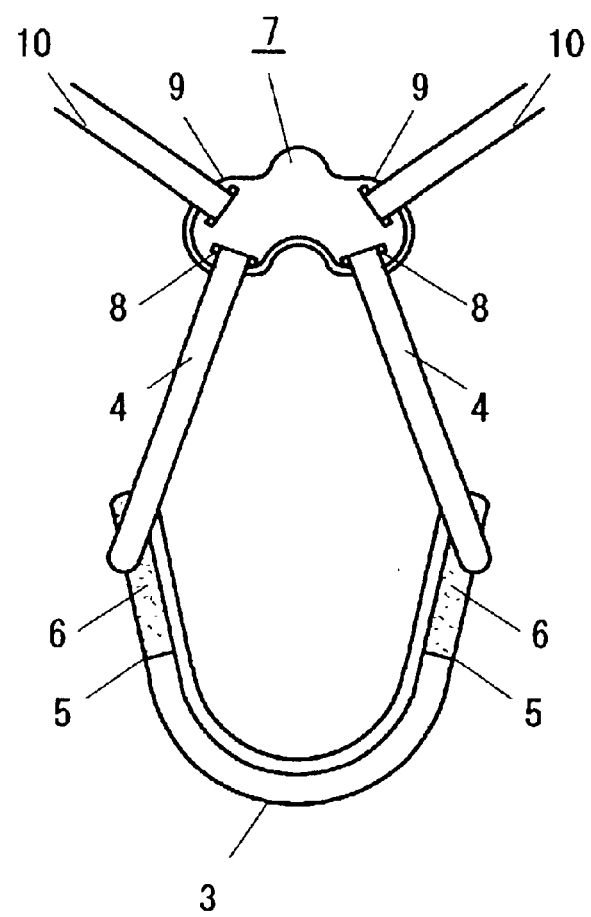
FIG. 2 is a perspective view of a lower jaw fitting piece of the same.

The other ends of the stoppers 4 are symmetrically stopped on a nasal mask-shaped or bridge-shaped holder 7 surrounding the nose as shown in FIG. 1 and FIG. 2 so as to push the lower jaw fitting piece 3 as mentioned above.

The holder 7 is constructed so that, as shown in FIG. 2, slit-shaped holding portions 8 and 9 are symmetrically formed at the upper and lower portions of both sides of the holder, the other ends of the abovementioned stoppers 4 of the lower jaw fitting piece 3 are connected to the lower holding portions 8, and soft hanging members 10 such as rubber belts or rubber straps to be hung on the ears or head are connected to the upper holding portions 9, whereby the lower jaw 2 can be pushed forward and held via the lower jaw fitting piece 3.

These tools and members can be formed from a hard material so as to maintain predetermined shapes, or can be formed from a soft material of silicone rubber or nonwoven fabric so as to make soft contact with the jaw and face while preventing contact discomfort even when a user rolls over during sleep.

Figure 3:
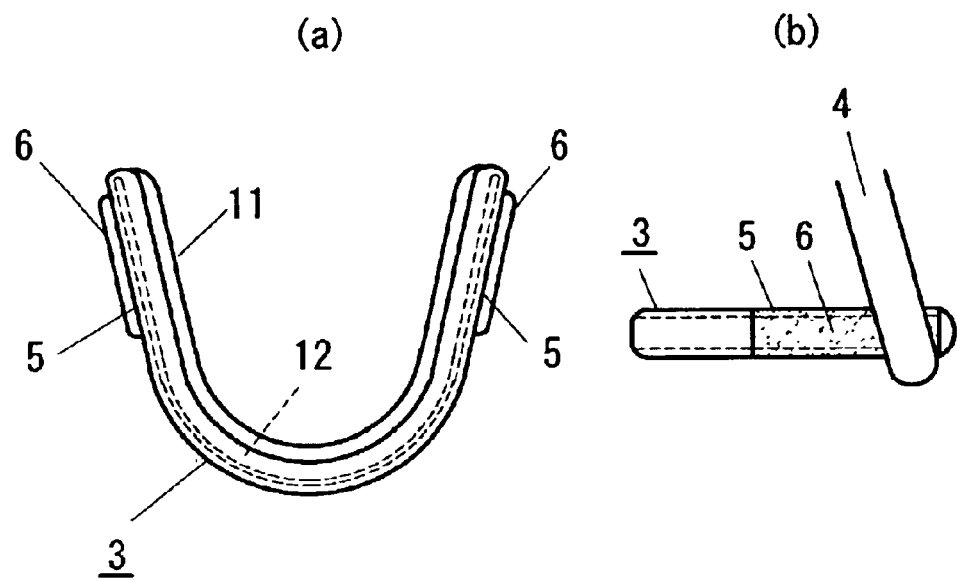
FIGS. 3(a) and (b) are a plan view and a side view of the lower jaw fitting piece of the same, including partial omission.

For example, it is possible that the lower jaw fitting piece 3 is resin-molded so as to closely fit the lower jaw of a user as shown in FIG. 3 and FIG. 4, and the contact surface and the circumferential surface of the lower jaw side of the molded piece are coated with a soft material 11 such as silicone rubber, a nylon resin, or an elastic material formed from high polymers with a predetermined thickness to achieve close fitting to the lower jaw 2.

Furthermore, as shown in FIG. 4, it is preferable that, a metal material such as thin aluminum with a 1 to 2 mm thickness, a thermoplastic resin of polypropylene, ABS, nylon, or polyurethane, and a thin hard material of engineering plastic such as polyimide or polyamide-imide is bent and inserted as a core material 12 of a mold for molding the lower jaw fitting piece 3 as shown in FIG. 4 and around them, a hard resin 13 is attached and a soft material 11 is coated, whereby the lower jaw fitting piece 3 is formed to be as light as possible and as thin as possible to an extent of 5 to 12 mm in total thickness.

Particularly, an aluminum plate is preferable since it can be easily bent along the lower jaw 2 of a user, and a plastic plate of a thermoplastic resin is also preferable since it can be easily bent and worked into a shape fitting the lower jaw 2 of a user by heating the plastic plate to a predetermined high temperature.

Furthermore, it is also possible that a soft material such as nonwoven fabric or a fabric material is stacked to a predetermined thickness to cover the core material 12 or is wound around the core material to form the lower jaw fitting piece 3.

The holder 7 can be formed into a mask shape or a bridge shape from silicone rubber, nonwoven fabric, or a fabric material so as not to cause discomfort to the jaw.

Figure 5:
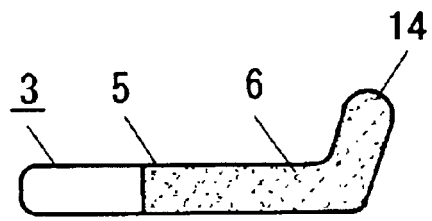
FIG. 5 is a partially omitted side view of another embodiment of the lower jaw fitting piece of the same.

Furthermore, as shown in FIG. 5, it is also possible that contact stopping portions 14 are projectedly provided in hook shapes at both ends of the lower jaw fitting piece 3 so as to be stopped on the rear edges of the lower jaw 2, whereby the lower jaw 2 can be pushed forward via the lower jaw fitting piece 3 as mentioned above.

Figure 6:
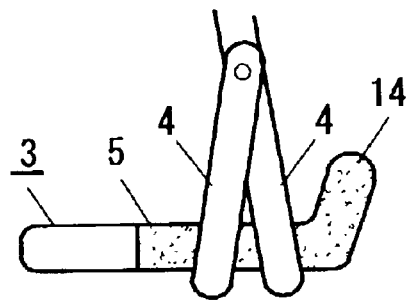
FIG. 6 is a partially omitted side view of still another embodiment of the lower jaw fitting piece of the same.

Furthermore, as shown in FIG. 6, it is possible that stopping portions 5 are broadly provided on the lower jaw fitting piece 3 and stoppers 4 are attached to a plurality of locations of the stopping portions so that the lower jaw fitting piece 3 is desirably pushed forward and held. By attaching the stoppers 4 at a plurality of locations, the lower jaw 2 can be more desirably and stably pushed forward via the lower jaw fitting piece 3.

Figure 7:
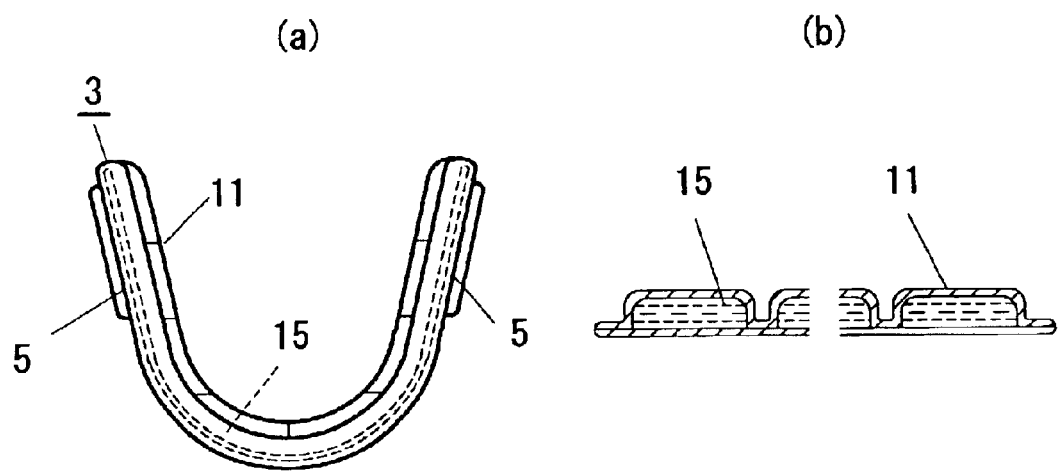
FIGS. 7(a) and (b) are a plan view of still another embodiment of the lower jaw fitting piece of the same and a partially omitted sectional view of a soft material.

Furthermore, as shown in FIG. 7(a) and FIG. 7(b), it is also possible that a soft material 11 which is formed into a pouched shape with a predetermined length and filled with a heat storage material, a cold insulator, or other high polymer gel materials 15 is detachably attached to the inner side contact portion of the lower jaw fitting piece 3 to the lower jaw 2. In this case, the main body of the lower jaw fitting piece is formed into a predetermined small, medium, or large size in advance and the soft material 11 is attached along the inner side of the lower jaw fitting piece 3 before use, and this is preferable since quick fitting is possible and soft contact to the lower jaw 2 of a user is achieved due to fluidity of the gel material 15. Particularly, it is preferable that the soft material 11 is partitioned in a quilting pattern as shown in the figure so as to evenly press the gel material 15 without dispersion.

Figure 8:
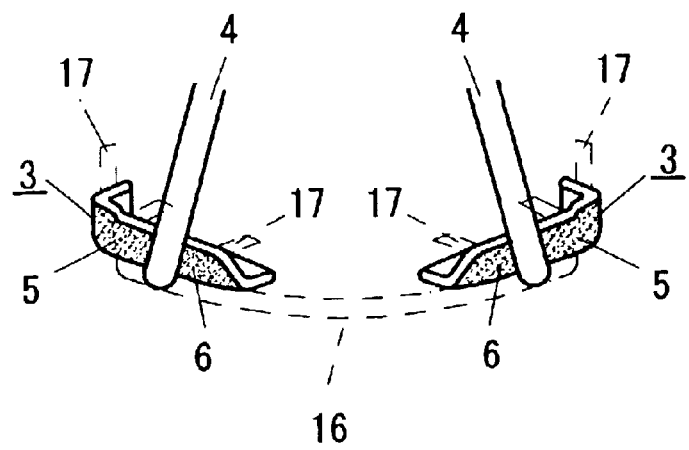
FIG. 8 is a partially omitted explanatory perspective view of still another embodiment of the same.

With the abovementioned construction, the lower jaw fitting piece 3 is roughly U-shaped so as to fit the entire lower jaw, however, as shown in FIG. 8, it is also possible that lower jaw fitting pieces are roughly L-shaped so as to be set on the rear edges of the lower jaw 2 in a fitting condition to prevent the lower jaw fitting pieces 3 from coming off the rear edges of the lower jaw 2 against pulling of the abovementioned stoppers 4.

For example, as shown in FIG. 8, right and left L-shaped lower jaw fitting pieces 3 are joined by an elastic material such as a rubber belt or rubber strap or a rigid joint material 16 such as a wire or a band of engineering plastic, and the lower jaw fitting pieces 3 are adhered to the face or lower jaw by a plurality of adhesives 17 such as adhesive tapes, whereby the abovementioned object that is to push the lower jaw 2 forward is achieved. Even for these lower jaw fitting pieces 3, the abovementioned structure can also be used.

Figure 9:
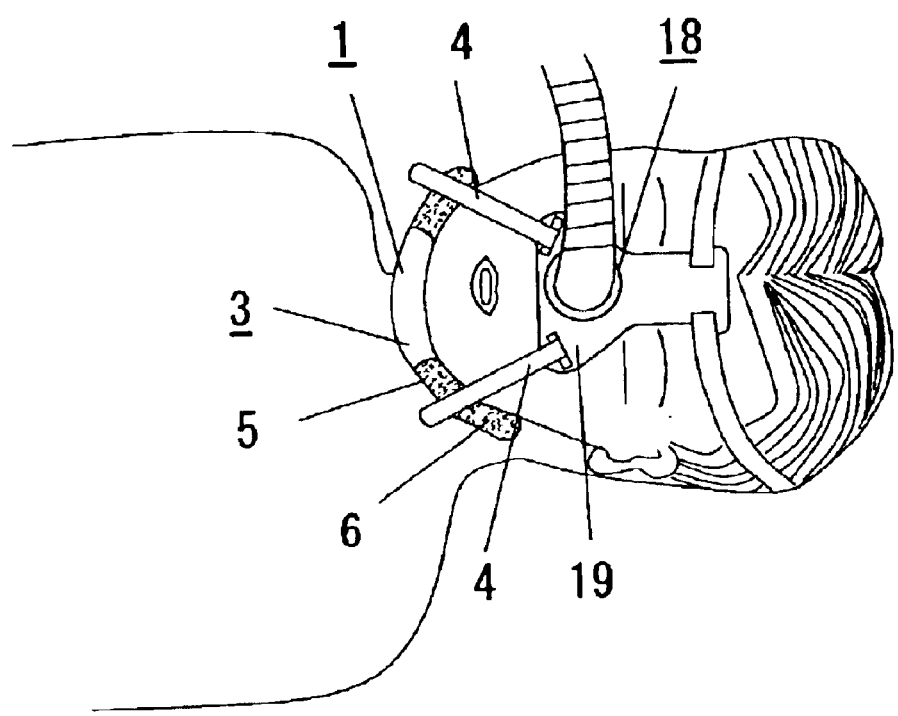
FIG. 9 is a plan view for explaining a condition of use of still another embodiment of the same.

FIG. 9 shows a construction in that the stoppers 4 of the abovementioned lower jaw fitting piece 3 are set on the mask 19 portion of positive pressure breathing apparatus 18 and the mask 19 portion is fixed, and the lower jaw fitting piece 3 is also fixed. Such use in combination with a positive pressure breathing apparatus is possible.

Furthermore, use in combination with a device for preventing sleep apnea constructed so as to fit appliances on the maxillary dentition and mandible dentition in an oral cavity is not excepted, and various uses are possible as necessary. Use in combination with such appliances can ease pain the corners of mandible caused by a forward pressing force applied to the lower jaw fitting piece.

Embodiments

FIG. 1 through FIG. 4 show an embodiment of the invention. Device 1 for preventing sleep apnea includes a lower jaw fitting piece 3 that is formed into a U-shape with a thickness of about 12 mm and a width (height) of about 25 mm along the lower jaw of a user so that the inner side is slightly inclined as shown in FIG. 1 through FIG. 4.

To form the jaw fitting piece 3, for example, as shown in FIG. 3 through FIG. 5, a hard material of an aluminum material with a predetermined length, thickness of 1 mm and a width (height) of 20 mm is used as a core material 12 and set in a mold that is molded by being bent along the lower jaw 2 of a user, and a quick-cure hard resin 13 is poured around the core material 12 in the mold and cured, and a soft material 11 of silicone rubber is coated on the outer circumference.

At this point, velvet fastener connecting means 6 are adhered to about 50 mm forward from the rear ends of the stopping portions 5 on both side surfaces of the lower jaw fitting piece 3, and lifting stoppers 4 of rubber belts having predetermined elasticity, a 1 mm thickness, and a 6 mm width are connected to predetermined positions on the connecting means 6 of the abovementioned stopping portions 5 via velvet fastener stopping pieces attached to the ends of the stoppers 4 by adjusting the tension.

The other end sides of the abovementioned stoppers 4 are attached to the right and left holding portions 8 at the lower side of the holder 7 that is bent and formed into a bridge shape along the nose as shown in FIG. 1 and FIG. 2, and hung on the head via hanging members 10 attached to the holding portions 9 at the upper side of the holder 7 as shown in FIG. 1 to fix the holder 7 on the nose, whereby the lower jaw fitting piece 3 can be pushed forward via the abovementioned stoppers 4. Furthermore, it is also possible that the lower jaw fitting piece 3 is pushed forward by hand and held as mentioned above.

As a result of trial use of the device 1 for preventing sleep apnea, which was thus manufactured as a trial item, snoring could be prevented, and a desired effect for preventing sleep apnea could also be obtained. Furthermore, the user could freely roll over during sleep and be conformable without skin discomfort since a soft material was used for portions in contact with the skin of the lower jaw and nose.

The forward pulling force of the lower jaw fitting piece 3 forward is 3 to 15 N (300 to 1500 gf) per one side, preferably 5 to 10 N (500 to 1000 gf) per one side, and it is preferable that the surface of the lower jaw fitting piece 3 coming into contact with the lower jaw 2 is set to have a surface pressure that does not cause biting of the lower jaw fitting piece 3 into the lower jaw or pain. Such a surface pressure is preferably adjusted to about 1 to 1.5 kPa (10 to 100 gf/cm$^2$).

The abovementioned construction is preferable since employment of detachable stopping means of velvet fasteners for the stopping portions and stoppers of the lower jaw fitting piece makes it easier to adjust the degree of pulling, angle of pulling, and positions of the stoppers, however, if the construction as shown in FIG. 6 is employed so that the lower jaw fitting piece 3 is pulled from a plurality of points of the stopping portions 5, the angle of pulling can be more easily adjusted, and this is effective.

Furthermore, as shown in FIG. 5 and FIG. 6, hook-shaped contact stopping portions 14 are provided at both ends of the lower jaw fitting piece 3 and set on the rear edges of the lower jaw 2, whereby the lower jaw fitting piece 3 can be effectively pushed forward.

Furthermore, it is also possible that a soft material 11 filled with a gel material 15 is adhered to the inner circumferential surface of the lower jaw fitting piece 3 by a predetermined adhesive. In this case, the main body of the lower jaw fitting piece is formed into a predetermined large, medium, or small size in advance, and this soft material 11 can be attached along the inner side of the lower jaw fitting piece 3 before use, and this is preferable since quick fitting is possible.

Furthermore, as shown in FIG. 8, it is also possible that lower jaw fitting pieces 3 are formed into roughly L-shaped grooves so as to be set on the lower jaw 2 in a fitting condition, the left and right L-shaped lower jaw fitting pieces 3 are joined by an elastic material such as a rubber band or rubber strap or a rigid material such as a wire or an engineering plastic band, or the lower jaw fitting pieces 3 can be adhered to the face or lower jaw by a plurality of adhesives 17 such as adhesive tapes. In this case, only the lower jaw rear edges are fixed, so that the burden on a user can be reduced.

Moreover, as shown in FIG. 9, it is also possible that the lower jaw fitting piece 3 of the abovementioned embodiment can be used in combination with a positive pressure breathing apparatus as mentioned above. This is effective since the stoppers 4 of the lower jaw fitting piece 3 are set on the mask 19 portion, whereby the lower jaw fitting piece 3 is fixed as well as the mask 19.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for preventing sleep apnea, wherein
   in order to prevent occurrence of apnea and snoring during sleep, stoppers having predetermined elasticity are attached to both right and left sides of a lower jaw fitting piece which fits a lower jaw,
   the stoppers being hung on a nose or on a face side of a head so as to push the lower jaw forward via the lower jaw fitting piece, wherein contact stopping portions are formed on both sides of the lower jaw fitting piece by bending rear ends of the lower jaw fitting piece into hook shapes for setting on rear edges of the lower jaws, wherein the lower jaw fitting piece is formed into a rough U shape along the lower jaw, and at least a portion of the lower jaw fitting piece making contact with the lower jaw is formed from a soft material, and stopping portions are provided at a side circumference of the lower jaw fitting piece to stop ends of the stoppers hung from the nose or the head, and wherein the stoppers are hung on the ears or the head through the nose via a holder so as to be tensioned.

2. The device for preventing sleep apnea according to claim 1, wherein the lower jaw fitting piece is formed to have a roughly L-shaped section so as to be set on the rear edges of the lower jaw in a fitting condition.

3. The device for preventing sleep apnea according to claim 2, wherein the stoppers having elasticity of the lower jaw fitting piece are hung on the ears or the head through the nose via a holder so as to be tensioned.

4. The device for preventing sleep apnea according to claim 1, wherein the lower jaw fitting piece includes an aluminum material, a thermoplastic resin, or an engineering plastic material.

5. The device for preventing sleep apnea according to claim 1, wherein the holder is formed into a nasal mask or a bridge surrounding the nose, slit-shaped holding portions are symmetrically provided at upper and lower portions of both sides of the holder, and the other ends of the above-mentioned stoppers of the lower jaw fitting piece are connected to the lower holding portions, and soft hanging members such as rubber belts or rubber straps to be hung on the ears and the head are connected to the upper holding portions.

6. The device for preventing sleep apnea according to claim 5, wherein a soft material which is formed into a pouched shape and filled with a heat storage material, a cold insulator, or other high polymer gel materials is attached to an inner side of the lower jaw fitting piece.

7. The device for preventing sleep apnea according to claim 1, wherein ends of the stoppers of the lower jaw fitting piece are set on a mask portion of a positive pressure breathing apparatus.

8. The device for preventing sleep apnea according to claim 1, wherein the lower jaw fitting piece is formed to have a roughly L-shaped section so as to be set on the rear edges of the lower jaw in a fitting condition.

9. The device for preventing sleep apnea according to claim 1, wherein the stoppers are belts or straps.

* * * * *